US008056718B2

(12) United States Patent
Howton

(10) Patent No.: US 8,056,718 B2
(45) Date of Patent: Nov. 15, 2011

(54) APPARATUS FOR STORING BABY BOTTLES

(76) Inventor: Soon Howton, Odessa, TX (US)

( * ) Notice: Subject to any disclaimer, the term of this patent is extended or adjusted under 35 U.S.C. 154(b) by 0 days.

(21) Appl. No.: 12/134,247

(22) Filed: Jun. 6, 2008

(65) Prior Publication Data

US 2009/0301915 A1 Dec. 10, 2009

(51) Int. Cl.
*B65D 65/00* (2006.01)
*A47B 73/00* (2006.01)
*A61L 2/00* (2006.01)

(52) U.S. Cl. ........... 206/427; 211/74; 312/408; 422/302

(58) Field of Classification Search .................. 206/427, 206/541–549; 211/74; 312/209, 31, 408, 312/210; 422/22, 28, 23–27, 29, 297–302, 422/303; 62/255, 457.1–457.9
See application file for complete search history.

(56) References Cited

U.S. PATENT DOCUMENTS 1,398,983 A * 12/1921 Ulrich ............................ 312/31
1,594,435 A * 8/1926 Vogt ............................ 312/305
2,844,141 A * 7/1958 Daugherty .................... 206/542
3,082,050 A * 3/1963 Baxter et al. .................. 312/209
3,358,845 A * 12/1967 Ising ............................... 211/74
4,669,790 A * 6/1987 Briggs ....................... 312/223.3
4,936,103 A * 6/1990 Newman ...................... 62/457.2
5,605,056 A * 2/1997 Brown et al. ................ 62/457.4
6,014,867 A * 1/2000 Floysvik ......................... 62/255
7,178,343 B2 * 2/2007 Linder ......................... 62/457.8
7,204,570 B2 * 4/2007 Benitsch et al. .............. 312/408
2003/0124024 A1 * 7/2003 Chang ........................... 422/299
2007/0003461 A1 * 1/2007 Kim .............................. 422/299

FOREIGN PATENT DOCUMENTS

FR 2600514 A1 * 12/1987

* cited by examiner

*Primary Examiner* — Bryon Gehman
(74) *Attorney, Agent, or Firm* — Michael Ries

(57) ABSTRACT

Disclosed is a storage apparatus for storing a plurality of baby bottles. Each of the plurality of baby bottles includes a bottle body and a set of components. The storage apparatus includes a first assembly. The first assembly includes a first compartment, and at least one tray removably configured within the first compartment. The at least one tray includes a plurality of receptacles capable of receiving and retaining the bottle body of the each of the plurality of baby bottles. Further, the storage apparatus includes a second assembly. The second assembly includes a support frame detachably configured to the first assembly, and a removable second compartment slidably coupled to the support frame. The removable second compartment is capable of storing the set of components of the each of the plurality of baby bottles.

13 Claims, 2 Drawing Sheets

APPARATUS FOR STORING BABY BOTTLES

FIELD OF THE INVENTION

The present invention relates generally to a baby care apparatus, and more specifically, to storage apparatus for storing baby bottles.

BACKGROUND OF THE INVENTION

Staying organized with various necessities of parenting is of prime significance while taking care of an infant or child. One such necessity is to have an organized storage system for keeping clean bottles that are required for feeding the infant or child. Such bottles that are used for feeding the baby child may hereinafter be referred to as, 'baby bottles.' Typically, a baby bottle includes a bottle body, and a set of components such as a bottle cap, a bottle nipple, and a bottle seal ring. In order to keep the bottle body and the set of components of the baby bottle at a suitable and an accessible location thereby preventing loss of the baby bottle, a storage system is required. Further, use of the storage system helps in preventing an unnecessary and a time-consuming search for the baby bottle when the baby child is crying out of hunger.

Moreover, such a storage system used for storing the baby bottles has become a crucial and an imperative tool employed by caretakers of childcare centers and large families where a large number of infants and children are looked after, and where problems of loss and mixing of the baby bottles are much more pronounced.

Accordingly, various storage systems have been employed for storing the baby bottles. However, conventional storage systems have not been able to efficiently cater to needs of a childcare center or a large family for storing a large number of baby bottles. For example, a conventional storage system includes a multi-purpose apparatus for storing and dispensing powdered baby formula, and for storing the baby bottles thereon. The multi-purpose apparatus includes a frame and a supporting means mounted on the frame for supporting at least one baby bottle thereon. Moreover, the multi-purpose apparatus includes a dispensing means configured to the frame for dispensing the powdered baby formula from within the multi-purpose apparatus. In addition, the multi-purpose apparatus includes a container for storing nipples of the baby bottles. However, due to employment of complex arrangement involving many components, the conventional storage system is heavy and cumbersome, and consumes a large amount of space while repositing as a complete functional unit. Moreover, the components of the complex arrangement acquire a lot of space within the conventional storage system and this may lead to unavailability of sufficient space for storing the baby bottles.

Similarly, many such other conventional storage systems are known to be cumbersome and provide an insufficient space for storing a large number of the baby bottles. Further, it becomes difficult to conveniently withdraw the baby bottles, prior to use for feeding purposes, from within the conventional storage systems that involve a high degree of complexity in their respective structural arrangements. Additionally, most of the conventional storage systems are not known to include a proper means for ventilation for storing washed baby bottles in a clean and dry form in order to prevent growth of mildew or any such microorganisms inside the baby bottles.

Accordingly, there is a need for an organized storage system that provides sufficiently large amount of space for storing baby bottles. Further, the storage system should serve as an easily accessible system for parents or caretakers to easily obtain the stored baby bottles when required for feeding purposes at any point of time. Furthermore, the storage system should be compact and light-weight, and should not consume a large amount of space while repositing as a complete functional unit. Additionally, the storage system should be provided with an adequate ventilation to prevent growth of mildew or any such microorganisms inside the baby bottles.

SUMMARY OF THE INVENTION

In view of the foregoing disadvantages inherent in the prior art, the general purpose of the present invention is to provide an organized storage system for storing baby bottles, which includes all the advantages of the prior art, and overcomes the drawbacks inherent therein.

Accordingly, an object of the present invention is to provide a light-weight, compact and easily-accessible storage system for storing baby bottles.

Another object of the present invention is to provide a storage system that is capable of storing a large number of baby bottles.

Still another object of the present invention is to provide a storage system for storing baby bottles wherein the storage system has provisions that help in preventing growth of mildew and any such microorganism inside the stored baby bottles.

In light of the above objects, the present invention discloses an organized storage system in the form of a storage apparatus for storing a plurality of baby bottles. Each of the plurality of baby bottles includes a bottle body and a set of components. The storage apparatus includes a first assembly. The first assembly includes a first compartment, and at least one tray removably configured within the first compartment. The at least one tray includes a plurality of receptacles capable of receiving and retaining the bottle body of each of the plurality of baby bottles. Further, the storage apparatus includes a second assembly. The second assembly includes a support frame detachably configured to the first assembly, and a removable second compartment slidably coupled to the support frame. The removable second compartment is capable of storing the set of components of the each of the plurality of baby bottles.

This together with other embodiments of the present invention, along with the various features of novelty that characterize the present invention, are pointed out with particularity in the claims annexed hereto and form a part of this disclosure. For a better understanding of the present invention, its operating advantages, and the specific objects attained by its uses, reference should be made to the accompanying drawings and the descriptive matter in which there are illustrated exemplary embodiments of the present invention.

BRIEF DESCRIPTION OF THE DRAWINGS

The advantages and features of the present invention will become better understood with reference to the following detailed description and claims taken in conjunction with the accompanying drawings, in which:

Like reference numerals refer to like parts throughout the description of the drawings.

DETAILED DESCRIPTION OF THE INVENTION

The exemplary embodiments described herein detail for illustrative purposes are subject to many variations in structure and design. It should be emphasized, however, that the present invention is not limited to a particular storage apparatus, as shown and described. It is understood that various omissions and substitutions of equivalents are contemplated as circumstances may suggest or render expedient, but these are intended to cover the application or implementation without departing from the spirit or scope of the claims of the present invention. Also, it is to be understood that the phraseology and terminology used herein is for the purpose of description and should not be regarded as limiting. The use of terms, "including," or "comprising," and variations thereof herein is meant to encompass the items listed thereafter and equivalents thereof as well as additional items. Further, the terms "a" and "an" herein do not denote a limitation of quantity, but rather denote the presence of at least one of the referenced item. Furthermore, the terms "first," "second," and the like, herein do not denote any order, quantity, or importance, but rather are used to distinguish one element from another.

The present invention provides a storage apparatus for storing a plurality of baby bottles in an organized manner. For the purpose of this description, each of the plurality of baby bottles includes a bottle body and a set of components. The term 'plurality of baby bottles,' as used herein refers to bottles used for feeding infants and children and may hereinafter be referred to as 'baby bottles'. Further, the term 'bottle body' refers to a part of each of the baby bottles that is capable of holding drinkable products used for feeding an infant or child. Suitable examples of the drinkable products for feeding the baby child include, but are not limited to, milk, water and juices. Further, the term 'set of components' refers to one or more parts of the each of the baby bottles that include a bottle cap, a bottle nipple, and a bottle seal ring.

Figure 1:
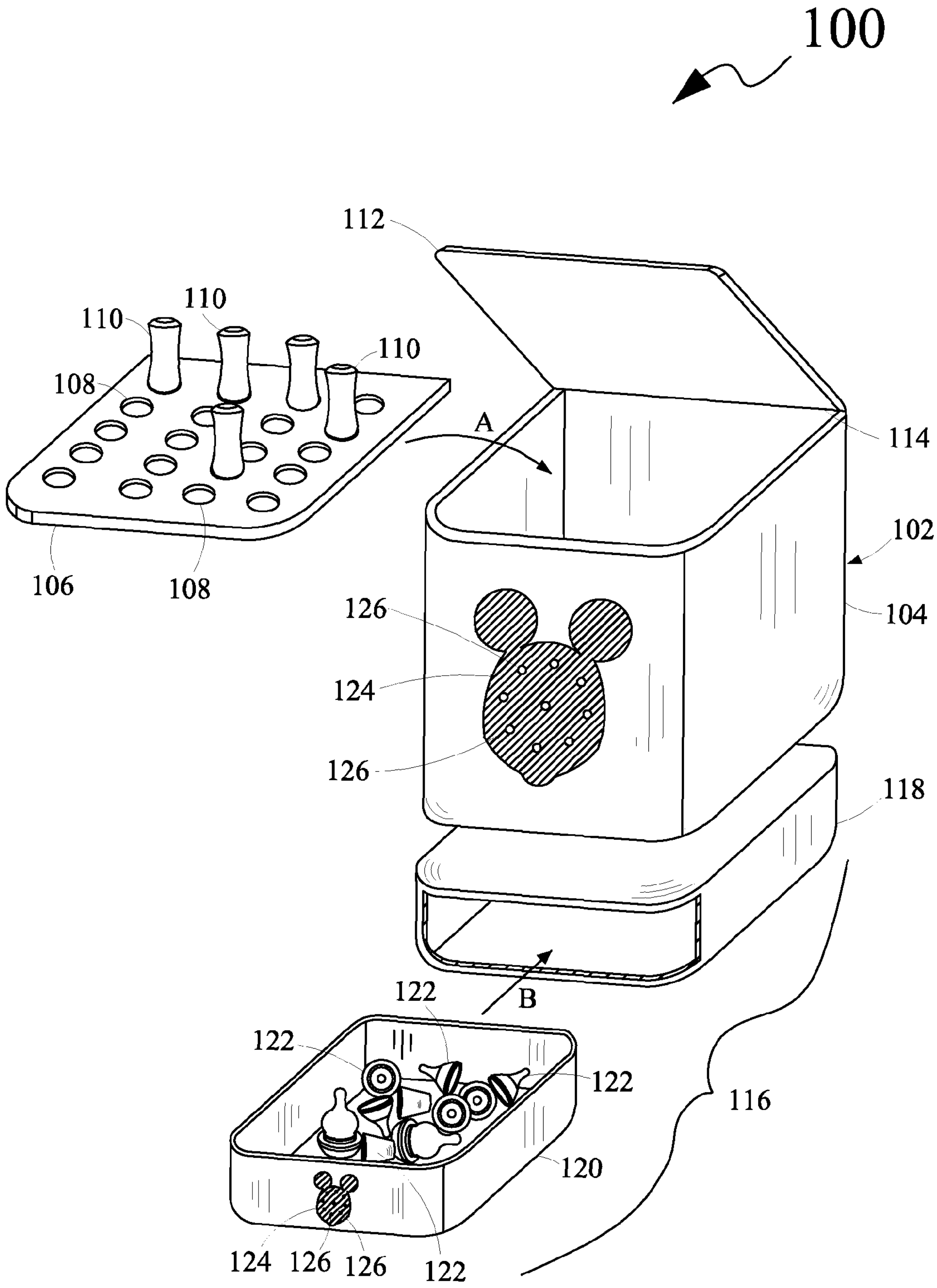
FIG. 1 depicts an unassembled view of a storage apparatus, such as storage apparatus 100, according to an exemplary embodiment of the present invention.
Figure 2:
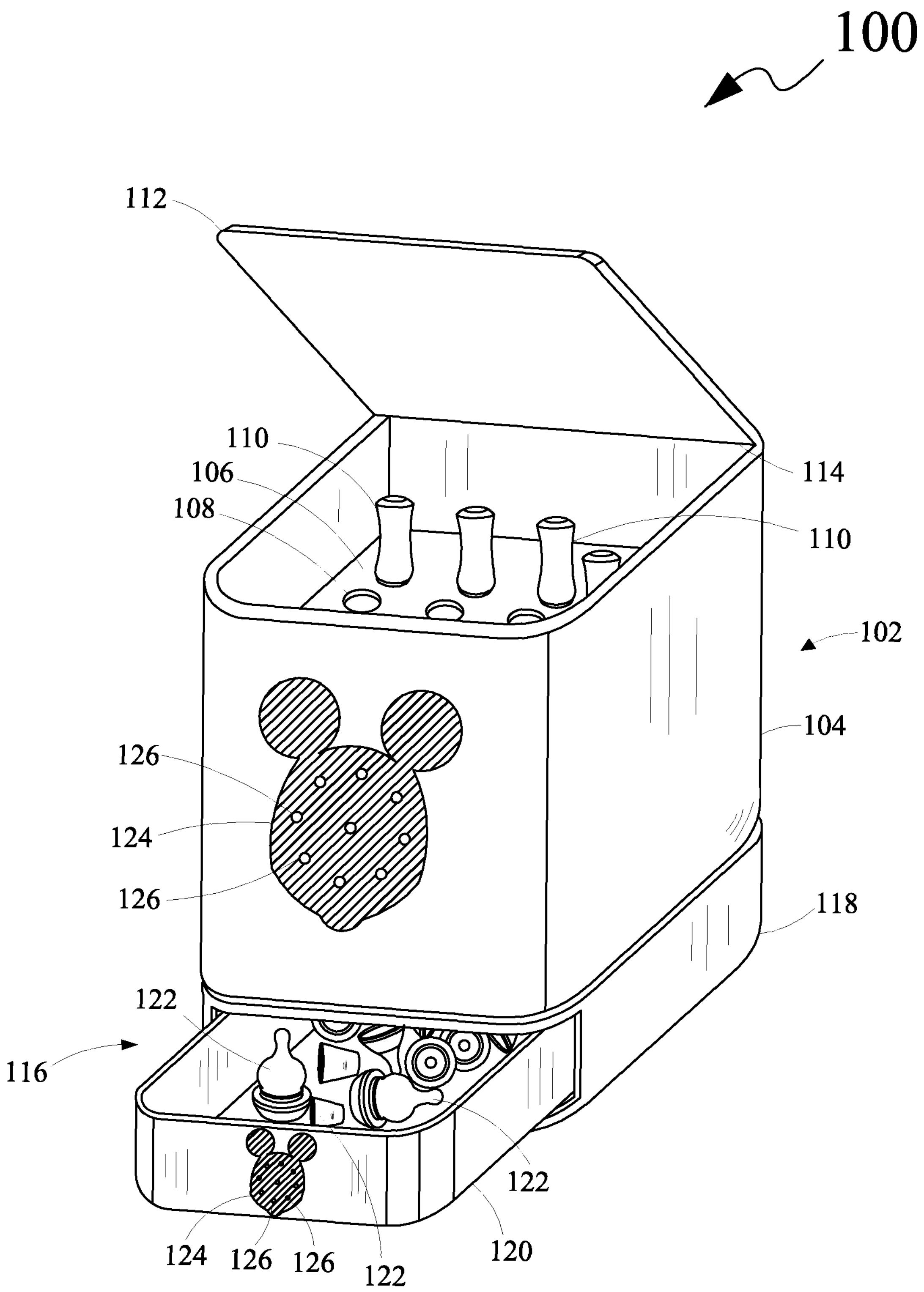
FIG. 2 depicts an assembled view of the storage apparatus 100, according to an exemplary embodiment of the present invention.

The storage apparatus for storing baby bottles, according to an exemplary embodiment, is explained in detail in conjunction with FIG. 1 and FIG. 2.

FIG. 1 depicts an unassembled view of the storage apparatus, such as storage apparatus 100, according to an exemplary embodiment of the present invention. Further, FIG. 2 depicts an assembled view of the storage apparatus 100, according to an exemplary embodiment of the present invention. As shown in FIG. 1, the storage apparatus 100 includes a first assembly 102. The first assembly 102 includes a first compartment 104 and at least one tray 106 (hereinafter referred to as a 'tray 106') that is capable of being removably configured within the first compartment 104.

For the purpose of this description, the first compartment 104 includes a bottom closed end (not shown) and a top open end (not shown). It should be understood that the first compartment 104 may be manufactured and designed as a container that is capable of holding the tray 106. Accordingly, the first compartment 104 may be of any shape, and dimension that allows the tray 106 to be easily and removably configured within the first compartment 104. In one embodiment of the present invention, the first compartment 104 is cubical in shape and has a specific dimension, which is characterized by a length of about 17 inches and a width of about 11 inches. As shown in FIGS. 1 and 2, it should be apparent that the specific dimension of the first compartment 104 solely contributes to a specific dimension of the first assembly 102.

Further, the first compartment 104 is a structurally strong and a light-weight compartment. Accordingly, the first compartment 104 may be made of a material such as wood, plastic, metal, paperboard, fiberboard, and the like. Furthermore, the first compartment 104 may be manufactured in a design that is aesthetically appealing to the baby child. Consequently, the first compartment 104 may be coated with vibrant colors that are appealing to an infant or child. More specifically, the first compartment 104 may be manufactured using a specific color depending on gender of the infant or child. Most often than not, such a color may be selected by parents or caretakers of the infant or child as they are aware of liking and disliking of the infant or child.

As shown in FIG. 1, the tray 106 is shown to be capable of being removably configured within the first compartment 104. More specifically, the tray 106 is shown to be capable of being removably configured within the first compartment 104 as illustrated by an arrow 'A' in FIG. 1. Even more specifically, such a tray 106 being removably configured within the first compartment 104 is shown in FIG. 2. However, it should be understood that the tray 106 may be removably configured within the first compartment 104 using a means for attachment. The means for attachment as used herein may refer to various means of attachments that are known in the art such as clamps, detachable screws, and the like.

The tray 106 includes a plurality of receptacles 108 that are capable of receiving and retaining bottle bodies 110 of the baby bottles. For the purpose of this description, the tray 106 is capable of receiving and retaining up to 32 bottle bodies, such as bottle bodies 110 of the baby bottles. However, it should be apparent that the tray 106 may include more than 32 receptacles, such as the plurality of receptacles 108, that are capable of receiving and retaining more than 32 of such bottles bodies 110. Further, each of the plurality of receptacles 108 is in the form of a hole that is capable of receiving and retaining a bottle body from the bottle bodies 110.

It should be understood that the plurality of receptacles 108 may possess shapes and dimensions that are complementary to shapes and dimensions of the bottle bodies 110 in order to properly receive and retain the bottle bodies 110 without causing slipping or falling-off of the bottle bodies 110. However, for the purpose of this description, the plurality of receptacles 108 is circular in shape having a diameter sufficiently large enough to hold the bottle bodies 110 that are cylindrical in shape.

Accordingly and without departing from the scope of the present invention, it should be understood that the tray 106 may be manufactured in standard or custom designs, dimensions and shapes in order to include the plurality of receptacles 108 that are complementary in shape and dimension to the standard or custom sized and shaped bottle bodies 110. Therefore, the tray 106 may be manufactured depending on a manufacturer's preferences or customers' demands in market, and accordingly may not be considered as limiting to the scope of the present invention.

Further, it should also be apparent to a person skilled in the art that the shape may vary depending on the shape of the first compartment 104. Examples of different shapes in which the tray 106 may be designed may include, but are not limited to, a rectangular shape, a circular shape, an oval shape. However, for the purpose of this description, the tray 106 is rectangular in shape. It should also be understood that the tray 106 may be of a dimension, which is equal to or sufficiently less than the dimension of the first compartment 104 so as the tray 106 may easily be configured within the first compartment 104 and may easily be removed from within the first compartment 104 whenever required. For example, the tray 106 may be required to be removed from within the first compartment 104 for washing and cleaning purposes. However, for the purpose of this description, the tray 106 has a dimension characterized by a length of about 17 inches, a width of about 11 inches, and a height of about 1⁄16 inches. Further, the tray 106 may be made of a variety of materials such as wood, plastic, metal, paperboard, fiberboard, and the like.

In addition to the first compartment 104 and the tray 106, the first assembly 102 may further include at least one flap 112 (hereinafter referred to as a 'flap 112') attached to the first compartment 104. More specifically, the flap 112 is attached to a portion 114 of the first compartment 104 to cover the top open end of the first compartment 104. Even more specifically, the flap 112 provides a covering to protect the bottle bodies 110 when retained by the plurality of receptacles 108 of the tray 106. Further, the flap 112 may be a foldable flap 112 capable of being folded. The flap 112 may be lifted-up in order to withdraw the bottle bodies 110 from within the first compartment 104 prior to use for feeding purposes.

It should be apparent to a person skilled in the art that the flap 112 may be an extended portion of the first compartment 104. Without departing from the scope of the present invention, it should also be understood that the first assembly 102 may include two flaps, such as flap 112, which are configured to form a double door flap arrangement.

The flap 112 may be manufactured in various shapes and dimensions. Further, it should be understood that the flap 112 may have a dimension sufficient enough to provide a suitable covering to the first compartment 104. For the purpose of this description, the flap 112 is rectangular in shape with a dimension, which is complementary to the dimension of the cubically-shaped first compartment 104. Moreover, the flap 112 may be manufactured using a variety of materials such as wood, plastic, metal, paperboard, fiberboard, and the like.

The above-described organized arrangement of the first assembly 102, as achieved by employing the tray 106 with the plurality of receptacles 108 within the first compartment 104, helps in retaining the bottle bodies 110 within a specified location thereby preventing loss of the bottle bodies 110. Further, the organized arrangement serves as an effective tool for providing an easy access to the bottle bodies 110 for use by the parents or the caretakers of the infant or child at any point of time when the infant or child may cry out of hunger.

As shown in FIG. 1, the storage apparatus 100 further includes a second assembly 116. The second assembly 116 includes a support frame 118 detachably configured to the first assembly 102. The support frame 118 may be detachably configured to the first assembly 102 using a means for attachment. The means for attachment may refer to various means for attachment that are known in the art. However, without departing from the scope of the present invention, it should be understood that the first assembly 102 may be stacked over the second assembly 116 through a direct contact with the support frame 118 without employing any means for attachment. More specifically, such a first assembly 102 stacked over the second assembly 116 through a direct contact with the support frame 118 without employing any means for attachment is shown in FIG. 2.

Further, the second assembly 116 includes a removable second compartment 120 that is slidably coupled to the support frame 118. It should be understood that the slidable coupling of the removable second compartment 120 with the support frame 118 enables an in-and-out sliding movement of the removable second compartment 120 with respect to the support frame 118 as shown by an arrow 'B' in FIG. 1. More specifically, such a removable second compartment 120 slidably coupled to the support frame 118 is shown in FIG. 2.

Further, it should be understood that the support frame 118 is manufactured in a specific design such that the support frame 118 is capable of enclosing the removable second compartment 120. Additionally, it should be understood that the removable second compartment 120 may be designed as a container, which is capable of storing a set of components 122 of the baby bottles. The set of components 122 include at least one of a bottle cap, a bottle nipple, and a bottle seal ring. Further, the removable second compartment 120 may be manufactured in various standard or custom shapes, and dimensions. For the purpose of this description, the removable second compartment 120 is cubical in shape. Further, the removable second compartment 120 has a specific dimension, which is characterized by a length of about 17 inches, a width of about 11 inches, and a height of about 2⅝ inches.

Further, the removable second compartment 120 may be similar to the first compartment 104 in terms of materials used for constructing a structurally strong, and a light-weight removable second compartment 120. Additionally, the removable second compartment 120 may be coated with the colors that may have been used for coating the first compartment 104.

Based on the specific dimensions of the first compartment 104 and the removable second compartment 120, as mentioned above, the storage apparatus 100 has an exemplary dimension, which is characterized by a length of about 17 inches, a width of about 11 inches, and a height of about 23⁄2 inches. Further, the storage apparatus 100 may weigh from about 1 to 2 pounds.

The above-described organized arrangement of the second assembly 116, as achieved by employing the removable second compartment 120 with the slidable coupling to the support frame 118, helps in retaining the set of components 122 within a specified location thereby preventing loss of the set of components 122. Further, the organized arrangement serves as an effective tool for providing an easy access to the set of components 122 for use by the parents or the caretakers of the infant or child at any point of time when the infant or child may cry out of hunger.

Moreover, to enhance the aesthetic appeal of the storage apparatus 100, the first compartment 104 and the removable second compartment 120 may include labels, such as labels 124. It should be apparent to a person skilled in the art that the labels 124 may be designed to represent shapes, figures, or symbols of cartoon characteristics or any such identification marks that are liked by infants or children.

Further, the storage apparatus 100 may include a plurality of apertures 126 (hereinafter referred to as 'apertures 126') for ventilation purposes. More specifically, each of the first compartment 104 and the removable second compartment 120 may include the apertures 126 for providing ventilation inside the storage apparatus 100. It should be understood that the ventilation inside the first compartment 104 and the removable second compartment 120 is necessary to prevent growth of mildew or any such microorganisms inside the bottle bodies 110 and the set of components 122. For the purpose of this description, the apertures 126 may be included in the labels 124.

Without departing from the scope of the present invention, it should be apparent that by way of storing the bottle bodies 110 of the baby bottles in the first assembly 102 and the set of components 122 in the second assembly 116, the present invention provides an effective, compact and organized means for storing the baby bottles at one location where the storage apparatus 100 may be reposited as a complete functional unit.

It should be apparent to a person skilled in the art that the storage apparatus 100 may also be used for storing Sippy cups (Sipster®) that are commonly employed for feeding infants and children.

Based on the foregoing, the present invention provides an effective storage apparatus for storing baby bottles in an organized arrangement. The above-disclosed arrangement of the storage apparatus provides a sufficiently large amount of space for storing a large number of the baby bottles at one point of time. Further, the storage apparatus serves as an easily accessible system for parents or caretakers to easily obtain the stored baby bottles when required for feeding purposes at any point of time. Furthermore, use of structurally strong and light-weighed materials for manufacturing various components of the storage apparatus results in obtaining a compact and a light-weight storage apparatus. Moreover, the compact nature of the storage apparatus helps preventing consumption of a large amount of space when the storage apparatus is reposited as a complete functional unit. Additionally, the storage apparatus provides adequate ventilation to prevent growth of mildew or any such microorganisms inside the baby bottles.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, and thereby enable others skilled in the art to best utilize the invention and various embodiments with various modifications as are suited to the particular use contemplated. It is understood that various omissions and substitutions of equivalents are contemplated as circumstances may suggest or render expedient, but such are intended to cover the application or implementation without departing from the spirit or scope of the claims of the present invention.

What is claimed is:

1. A storage apparatus to vertically store a plurality of baby bottles each bottle comprising a bottle body, and a set of components, comprising:

a first assembly that includes a first compartment with a flap attached to a portion of the first compartment to cover the vertically stored baby bottles and enclose the first compartment, and at least one tray removably configured within the first compartment, the at least one tray includes a plurality of receptacles that are each generally circular in shape and capable of vertically receiving and retaining the bottle body of each of the baby bottles in an upright disposition;

a second assembly that includes a support frame detachably configured to the first assembly, and a removable second compartment slidably coupled to the support frame, wherein the removable second compartment is capable of storing the set of components of each of the baby bottles, wherein the removable second compartment includes a first plurality of apertures to ventilate the second compartment.

2. The storage apparatus of claim 1, wherein the set of components include at least one of a bottle cap, a bottle nipple and a bottle seal ring.

3. The storage apparatus of claim 1, wherein the first compartment includes a second plurality of apertures to ventilate the first compartment.

4. The storage apparatus of claim 1, wherein the first apertures are formed in a portion of the second compartment that provide ventilation to an inner portion of the second compartment.

5. The storage apparatus of claim 4, wherein the first assembly is stacked over the second assembly.

6. The apparatus according to claim 1, wherein the first compartment is made of material selected from the group consisting of wood, plastic, metal, paperboard and fiberboard.

7. The apparatus according to claim 1, wherein the flap is made of material selected from the group consisting of wood, plastic, metal, paperboard and fiberboard.

8. The apparatus according to claim 1, wherein the storage apparatus weights approximately 1 to 2 pounds.

9. A storage apparatus to vertically store a plurality of baby bottles, each bottle comprising a bottle body, and a set of components, comprising:

a first assembly that includes a first compartment, with at least one flap attached to a portion of the first compartment and a plurality of first apertures to ventilate the first assembly, and at least one tray removably configured within the first compartment, the at least one tray includes a plurality of receptacles that are each generally circular in shape and capable of vertically receiving and retaining the bottle body of each of the baby bottles in an upright disposition; and a second assembly that includes a support frame detachably configured to the first assembly, and a removable second compartment slidably coupled to the support frame, wherein the removable second compartment is capable of storing the set of components of each of the baby bottles, and wherein the removable second compartment includes a plurality of second apertures to ventilate the second compartment.

10. The storage apparatus of claim 9, wherein the second apertures are formed in a portion of the second compartment where the second apertures provide a ventilation path from an inner portion of the second compartment to outside the storage apparatus.

11. The apparatus according to claim 9, wherein the first compartment is made of material selected from the group consisting of wood, plastic, metal, paperboard and fiberboard.

12. The apparatus according to claim 9, wherein the flap is made of material selected from the group consisting of wood, plastic, metal, paperboard and fiberboard.

13. The apparatus according to claim 9, wherein the storage apparatus weights approximately 1 to 2 pounds.

* * * * *